United States Patent [19]
Mallory et al.

[11] Patent Number: 5,552,704
[45] Date of Patent: Sep. 3, 1996

[54] EDDY CURRENT TEST METHOD AND APPARATUS FOR MEASURING CONDUCTANCE BY DETERMINING INTERSECTION OF LIFT-OFF AND SELECTED CURVES

[75] Inventors: Chester L. Mallory, Campbell; Walter Johnson, San Jose; Kurt Lehman, San Mateo, all of Calif.

[73] Assignee: Tencor Instruments, Mountain View, Calif.

[21] Appl. No.: 82,661

[22] Filed: Jun. 25, 1993

[51] Int. Cl.$^6$ ............ G01R 33/00; G01R 33/12; G01N 27/76; G01N 27/72
[52] U.S. Cl. ............ 324/233; 324/225; 324/202; 324/236
[58] Field of Search ............ 324/225, 234, 324/237–243, 202, 236, 650, 654, 655, 693, 709, 714

[56] References Cited

U.S. PATENT DOCUMENTS

| | | | |
|---|---|---|---|
| 4,000,458 | 12/1976 | Miller et al. | 324/34 |
| 4,302,721 | 11/1981 | Urbanek et al. | 324/226 |
| 4,351,031 | 9/1982 | Flaherty et al. | 324/225 |
| 4,528,856 | 7/1985 | Junker et al. | 73/779 |
| 4,727,322 | 2/1988 | Lonchampt et al. | 324/229 |
| 4,849,694 | 7/1989 | Coates | 324/230 |

OTHER PUBLICATIONS

Miller et al., "Contactless Measurement of Semiconductor Conductivity by Radio–Free–Carrier Power Absorption," Rev. Sci. Instrum., V. 47, No. 7, pp. 799–805 (Jul. 1976).
Jeanneret et al., "Inductive Conductance Measurements in Two–Dimensional Superconducting Systems," Applied Phys. Lett. 55 (22), pp. 2336–2338 (Nov. 27, 1989).
Excerpt from "Nondestructive Testing Handbook," Second Edition, edited by R. C. McMaster, American Society for Nondestructive Testing, Inc. (1986), vol. 4–Electromagnetic Testing, pp. 218–222.
One–page advertisement (from the Jun. 1989 issue of the publication "Quality") by Zetec.
Soviet Inventions Illustrated, E1 section, week 8643, (abstract of SU1221–572–A), Dec. 3, 1986, pp. 14–15.

Primary Examiner—Walter E. Snow
Attorney, Agent, or Firm—Limbach & Limbach L.L.P.; Alfred A. Equitz

[57] ABSTRACT

A method and apparatus for performing conductance measurements on a sample using an eddy current probe, without the need for measurement or knowledge of the separation between probe and sample. The probe comprises sense and drive coils mounted in close proximity to each other (or a single coil which functions as both a sense and drive coil), circuitry for producing AC voltage in the drive coil, and a meter for measuring in-phase and quadrature components of induced voltage in the sense coil. Look-up table data can be generated for use in subsequent measurements on samples of unknown conductance by performing eddy current measurements on samples having different known conductances to generate reference lift-off curves, processing the reference lift-off curves to determine a conductance function relating each known conductance to a location along a selected curve, and storing conductance values determined by the conductance function for different points on the selected curve as the look-up table data. An unknown sample conductance can then be determined by generating a lift-off curve from voltage measurements at different probe separations from the sample, determining a new intersection voltage pair representing the intersection of the lift-off curve with the selected curve, and determining the unknown conductance as a look-up table value indexed by the new intersection voltage pair.

30 Claims, 6 Drawing Sheets

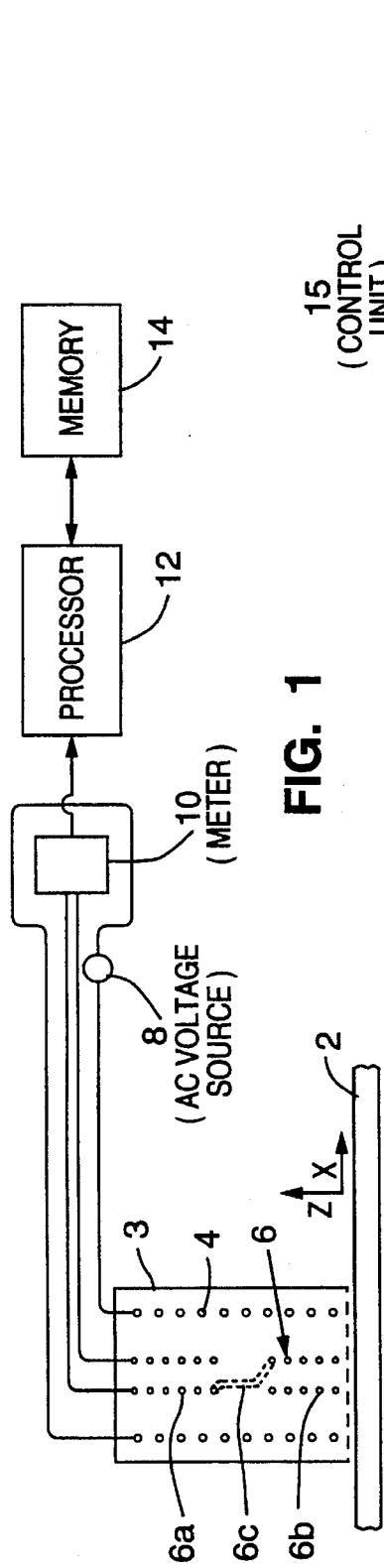
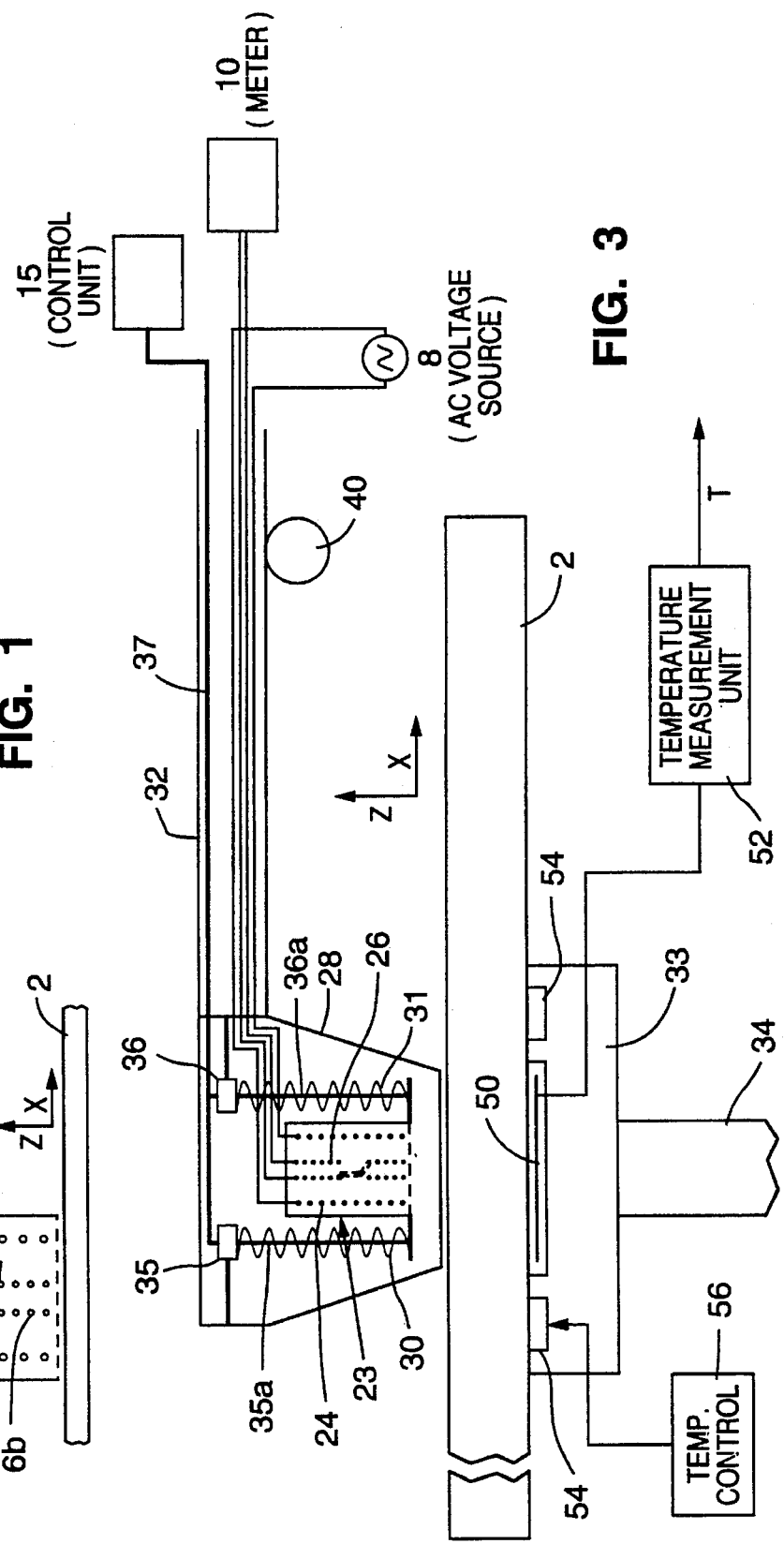

EDDY CURRENT TEST METHOD AND APPARATUS FOR MEASURING CONDUCTANCE BY DETERMINING INTERSECTION OF LIFT-OFF AND SELECTED CURVES

FIELD OF THE INVENTION

The invention pertains to methods and apparatus for performing eddy current testing and processing eddy current test data, and for measuring the conductance or conductivity of a sample (such as a semiconductor wafer).

BACKGROUND OF THE INVENTION

For a variety of commercially significant purposes it is desirable to perform nondestructive tests to measure the electrical conductance, conductivity, or resistivity of a sample.

For example, during semiconductor product manufacturing, there is a need to measure the conductivity of various conductive thin films on semiconductor wafers and integrated circuits in a nondestructive manner. Also during semiconductor product manufacturing, it is useful to perform stress measurements on semiconductor wafers and integrated circuits in a nondestructive manner.

It is well known that such measurements can be obtained by eddy current testing. One conventional apparatus for performing eddy current testing on a sample is described in U.S. Pat. No. 4,000,458, issued Dec. 28, 1976. Another is described in Jeanneret, et al., "Inductive Conductance Measurements in Two-Dimensional Superconducting Systems," Applied Phys. Lett. 55 (22), pp. 2336–2338 (Nov. 27, 1989). The Jeanneret, et al., apparatus employs two coils, both positioned above the sample: a drive coil (of radius 2.05 mm), and an astatically wound receiver coil (having radius 1.2 mm) coaxially mounted within the drive coil. The receiver coil has a first section (wound with right-handed helical geometry) and a second section (wound with left-handed helical geometry). The lower end of the drive coil is positioned at a first known distance (0.3 mm) above the sample, and the lower end of the lower section of the receiver coil is positioned at a second known distance above the sample, where the second distance is much (e.g., an order of magnitude) smaller than the first distance. As the drive coil is driven by an AC voltage source (at a frequency of 70 kHz), the in-phase and quadrature components of the voltage at the receiver coil are measured by "conventional lock-in techniques or by an ac mutual-inductance bridge." The resulting voltage data can be processed (with data indicating the coils' distance from the sample) to determine the sample's complex conductance.

Several conventional techniques for processing in-phase and quadrature voltage data obtained during eddy current testing are described in the *Nondestructive Testing Handbook, Second Edition,* edited by R. C. McMaster, American Society for Nondestructive Testing, Inc. (1986), Volume 4 -Electromagnetic Testing, at pages 218–222. However, such conventional techniques require accurate knowledge of the separation between the sample and an eddy current probe (comprising drive coil and sense coil) at one or more positions of the probe relative to the sample.

In typical applications of eddy current testing, accurate measurement (or prior knowledge) of the separation between the eddy current probe and the sample requires complicated and expensive equipment. For example, U.S. Pat. No. 4,302,721 describes an eddy current testing apparatus which employs complicated acoustic wave measurement equipment to measure eddy current probe-to-sample separation.

Other typical applications of eddy current testing require maintenance of the eddy current probe at a constant, precisely repeatable, distance from the sample. For example, U.S. Pat. No. 4,849,694, issued Jul. 18, 1989, assumes that a sample's resistivity or thickness is known, and employs eddy current measurements to determine the other of the sample's resistivity or thickness in a manner requiring that the measurement apparatus maintain the eddy current probe at a constant, precisely repeatable distance "d" from the sample surface. This reference teaches that a precision optical microscope is preferably used to precisely position the eddy current probe at the distance "d" from the sample.

Until the present invention, it was not known how to perform eddy current testing to obtain accurate conductance or conductivity measurements on a sample without the need to measure the separation between the probe and the sample or to perform measurements at a precisely maintained probe-to-sample separation. The eddy current testing method of the present invention provides a convenient and inexpensive way to obtain conductance and/or conductivity measurements on a sample without the need to measure separation between an eddy current probe and a sample.

SUMMARY OF THE INVENTION

The inventive apparatus is capable of performing conductance (or conductivity, resistance, or resistivity) measurements on a sample using an eddy current probe without the need to measure (or otherwise know) the separation between the probe and sample. Preferably, the apparatus includes an eddy current probe comprising a housing, and at least one drive coil and at least one sense coil mounted within the housing. Each sense coil is mounted in sufficiently close proximity to a drive coil (or coils) to allow mutual inductance measurements. In a preferred embodiment, one drive coil is mounted in the housing, and one sense coil is mounted in the housing coaxially with the drive coil. In other embodiments, a single coil functions both as a drive coil and a sense coil.

The apparatus also includes means for producing AC voltage in the drive coil (preferably with a selected frequency in the range from 100 KHz to 100 MHz or higher), a meter for measuring the amplitude of both the in-phase component and the quadrature component of the induced AC voltage in a sense coil (or coils) in response to AC voltage in the drive coil, and a processor (with a memory) for processing the output signal from the meter.

Preferred embodiments of the inventive method include the steps of generating and storing look-up table data for use in subsequent measurements on samples having unknown conductivity. The first step of the look-up table data generation process is to perform eddy current measurements on samples having known resistivity to generate reference lift-off curves. The reference lift-off curve for each sample is generated by measuring sense coil voltage pairs (each pair comprising an in-phase and a quadrature component of an AC voltage induced in a sense coil in response to AC voltage in a drive coil) for each of several probe positions along an axis normal to the sample surface. The separation between the sample and the probe need not be measured or otherwise known. For each sample, several measured sense coil voltage pairs are processed to determine a reference lift-off curve.

A processor then processes the reference lift-off curves to determine a set of intersection voltage pairs, each pair representing the intersection of a selected curve (e.g., a circular arc or another graph of a polynomial function) with a different one of the reference lift-off curves. The processor then determines a resistivity function which relates the known resistivity associated with each intersection voltage pair to a location along the selected curve. The resistivity function determines a resistivity value for each point on the selected curve (or a resistivity value for each point on the selected curve), including resistivity values not associated with any of the reference lift-off curves. The processor then stores a look-up table comprising a resistivity value determined by the resistivity function, for each of a number of different points on the selected curve. Each resistivity value can be retrieved from the stored look-up table by accessing a memory location indexed by a corresponding index voltage pair.

After storing the look-up table, the resistivity of an "unknown" sample can be determined in accordance with the invention in the following manner. A lift-off curve is generated by producing an AC voltage in the drive coil while measuring both in-phase and quadrature components of the AC voltage induced in the sense coil, for each of a number of probe positions along an axis normal to the surface of the unknown sample. As during reference lift-off curve generation, the separation between the sample and the probe (along the z-axis) need not be measured or otherwise known. The measured sense coil voltage pairs (each pair comprising an in-phase voltage and a quadrature voltage) are processed to determine a lift-off curve. The processor next determines a "new" intersection voltage pair which represents the intersection of the lift-off curve (for the unknown sample) with the selected curve employed during look-up table generation, and identifies the resistivity of the unknown sample as a look-up table value it retrieves from the memory location indexed by the new intersection voltage pair.

In alternative embodiments, software for implementing the resistivity function itself can be stored in a memory (rather than the described look-up table). In such alternative embodiments, the resistivity of an unknown sample is determined in the same way described above, except that rather than retrieving a stored look-up table value after generating a "new" intersection voltage pair for the unknown sample, the processor determines the resistivity of the unknown sample by processing the new intersection voltage pair in accordance with the resistivity function.

In a class of preferred embodiments, the inventive apparatus processes data obtained with very high drive coil frequency (e.g., from 100 KHz to 100 MHz or higher) and a very small diameter probe (very small diameter drive and sense coils), to measure very small sample regions. Very thin layers of a multilayer sample can be selectively measured by exploiting the phenomenon that, for a given probe, the depth of the sample region measured depends in a well understood manner on the frequency of the AC voltage in the drive coil.

BRIEF DESCRIPTION OF THE DRAWINGS

FIG. 1 is a simplified schematic diagram of a preferred embodiment of the inventive apparatus.

FIG. 3 is a simplified side cross-sectional view of a portion of second preferred embodiment of the inventive apparatus.

DETAILED DESCRIPTION OF THE PREFERRED EMBODIMENT

Figure 2:
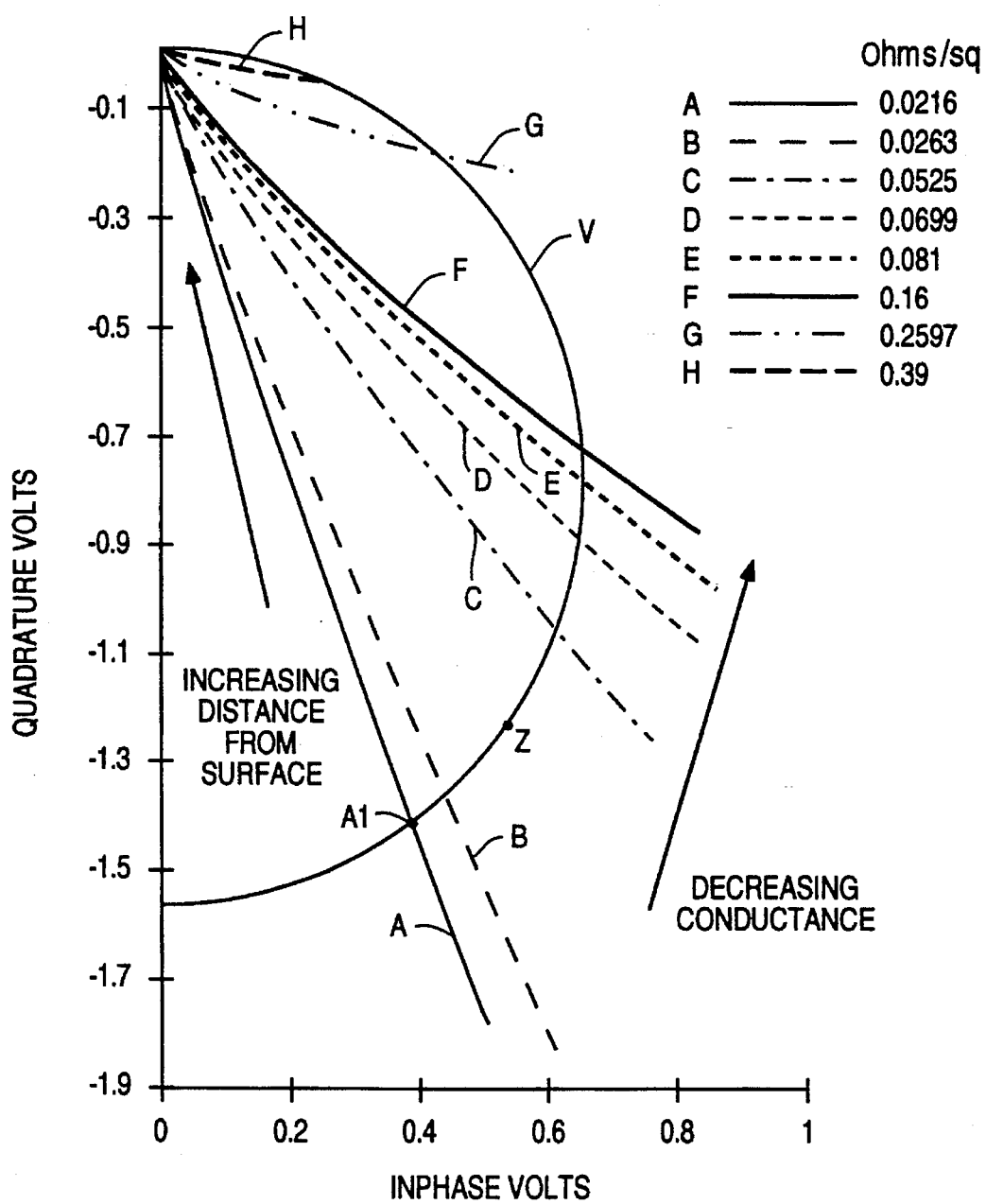
FIG. 2 is a graph of eight lift-off curves, and a circular arc intersecting the lift-off curves, generated in accordance with the look-up table generation operation of the invention.

Since electrical resistivity is the inverse of electrical conductivity, determination of either of these quantities in accordance with the invention determines both of them. Although for simplicity, the invention is described herein with reference to embodiments which determine a sample's electrical conductivity, it will be apparent to those of ordinary skill in the art how to implement variations on these embodiments to determine electrical resistivity in accordance with the invention. It will also be apparent to those of ordinary skill in the art how to implement variations on these embodiments to determine complex electrical conductance, resistance, sheet conductance, or sheet resistance. For example, electrical resistance can be determined by measuring electrical resistivity using the described apparatus, independently measuring a linear dimension of the sample by any conventional means, and dividing the measured resistivity by the measured linear dimension to determine the resistance. In the claims and the abstract, the term "conductance" is used in a broad sense to denote conductivity, resistivity, conductance, resistance, sheet conductance, or sheet resistance.

The expression "AC voltage" is used throughout the specification, including in the claims, to denote any periodically time-varying voltage, including for example, voltages having sinusoidal, square wave, or sawtooth waveforms.

A preferred embodiment of the inventive apparatus will described with reference to FIG. 1. As shown in FIG. 1, the apparatus includes an eddy current probe comprising housing 3, drive coil 4 mounted within housing 3, and sense coil 6 (comprising sections 6a, 6b, and 6c) within housing 3. Sense coil 6 is mounted coaxially with coil 4, has a smaller radius than coil 4, and is an astatically wound coil which comprises: first section 6a wound with a first handedness (e.g. section 6a can be a right-handed helix), second section 6b wound with the opposite handedness (e.g. section 6b is a left-handed helix if section 6a is a right-handed helix), and a non-wound central section 6c which connects sections 6a and 6b.

In some preferred embodiments, each coil is wound on a core of high permeability ferrite material. In other preferred embodiments, each coil is wound on a core of acrylic material.

In a preferred embodiment, coil 4 comprises 36 gauge copper wire having 40 turns with a spacing substantially equal to the diameter of the wire between turns and a radius in the range from 6 mm to 10 mm, and each of coil sections 6a and 6b comprises 38 gauge copper wire having 18 turns with a spacing substantially equal to the diameter of the wire between turns and a radius in the range from 1 mm to 3 mm. In this embodiment, the non-wound central section 6c has a length of 4 mm.

In alternative embodiments, the probe can include more than one sense coil, more than one drive coil, or both. In all embodiments which include at least one drive coil and at least one sense coil, each drive coil is mounted in sufficiently close proximity to a sense coil to allow mutual inductance measurements (but each sense coil need not be mounted coaxially with a drive coil). Alternatively, the probe can include a single coil, which functions as both a drive coil and a sense coil.

In FIG. 1, the "z" direction is normal to sample 2's top surface, and the "x" direction is parallel to sample 2's top surface. A linear actuator (such as that described below with reference to FIG. 3) is provided for translating housing 3 (and/or coil 4) in the "z" direction relative to sample 2, to enable measurements with the lower end of coil 4 in any of a range of positions (along the z-axis) above sample 2. Alternatively, the sample can be moved relative to fixed coils.

The term "above" is employed herein to denote a direction normal to the sample surface (or normal to a portion of the sample surface); not to denote any particular direction relative to the earth's surface.

In some embodiments, housing 3 (and/or coil 4) can be positioned in direct contact with sample 2's surface as well as in positions separated from sample 2, but in other embodiments housing 3 (and/or coil 4) is not positionable in direct contact with sample 2. It is unnecessary for the FIG. 1 apparatus to include a means for determining the actual position of housing 3 (or coils 4 and 6) along the z-axis relative to sample 2.

Preferably, a linear actuator is provided for translating coil 6 relative to coil 4, so that when coil 4 is in a first position (for making a conductivity measurement), coil 6 can be translated into an optimal position relative to coil 4 for optimizing the eddy current probe's sensitivity.

AC voltage source 8 is connected to coil 4. When activated, source 8 produces AC voltage in coil 4 with a selected frequency within the range from 100 KHz to at least 100 MHz (or the range from 1 MHz to at least 100 MHz). In a typical case in which coil 4 (and associated electrical lines) represents a load of 50 ohms to source 8, source 8 is capable of producing sinusoidal voltage having a peak-to-peak amplitude of about five volts in coil 4. To increase the probe's resolution, thereby allowing measurement of the conductance of smaller sample regions (either at the sample surface or at selected depths below the sample surface), the diameters of drive coil 4 and sense coil 6 should be reduced and the AC voltage frequency in drive coil 4 increased.

Desired thin layers of a multilayer sample can be selectively measured because, for a given probe, the depth of the sample region measured depends in a well understood manner on the AC voltage frequency in drive coil 4. The drive coil voltage frequency can be chosen to cause the electromagnetic field due to the drive coil to extend to a desired depth in the sample.

For a given separation between the lower end of coil 4 and sample 2 (and the lower end of coil 6 and sample 2), the amplitude of the AC voltage induced in sense coil 6 in response to AC voltage in coil 4 will depend on the conductance of sample 2. Meter 10, which is connected to coil 6, measures the amplitude of both the in-phase component and the quadrature component (the component 90 degrees out of phase with the voltage in drive coil 4) of the induced AC voltage in sense coil 6. In preferred embodiments, meter 10 is a vector voltmeter having sensitivity in the range from 1 millivolt to 100 millivolts over the frequency range of the drive coil voltage (typically from 100 kHz to at least 100 MHz). The output signal from meter 10, preferably a digital signal indicative of the amplitudes of both the in-phase and quadrature components of the induced voltage in coil 6, undergoes processing in accordance with the invention in processor 12 (in a manner to be described below). In alternative embodiments, the in-phase and quadrature components of the induced voltage in coil 6 are measured using an AC mutual-inductance bridge. Processor 12 is preferably a general purpose digital computer programmed with software for generating the data signals described herein (for example signals indicative of the below-described conductance function, and signals indicative of the below-described conductivity or resistivity values), and for storing data in (and retrieving stored data from) memory 14 connected thereto.

A preferred embodiment of the inventive method will next be described with reference to FIG. 2. The first step of the method is to generate look-up table data (by operating processor 12) and store the data (in memory 14) as a look-up table for use in subsequent measurements on samples having unknown conductivity.

The first step of the look-up table data generation process is to perform eddy current measurements on each of a number of samples (N samples) having known conductivity, to generate a corresponding number of lift-off curves (N lift-off curves). Eight such lift-off curves are shown in FIG. 2.

Each lift-off curve is generated by producing an AC voltage in drive coil 4 while measuring both the in-phase and quadrature components of the AC voltage induced in sense coil 6, for each of a number of probe positions along the z-axis. The separation between the sample and the probe (along the z-axis) need not be measured or otherwise known.

Typically, a small number (such as twenty-five) of sense coil voltage pairs (each pair comprising an in-phase voltage and a corresponding quadrature voltage) are measured (using meter 10) for each sample. Each sense coil voltage pair is measured with a different probe position along the z-axis with respect to the sample. For each sample, a set of measured sense coil voltage pairs is processed to determine a lift-off curve.

Specifically, for a given sample, processor 12 processes an output signal from meter 10 (indicative of a sense coil voltage pair) for each of several probe positions to determine a polynomial function (a function of "in-phase" voltage versus "quadrature" voltage) which best fits the data. This function determines the lift-off curve for the sample.

An example of such a lift-off curve is the curve labeled "A" in FIG. 2. Lift-off curve A is determined by processing a number of sense coil voltage pairs (e.g., seven sense coil voltage pairs) obtained by measuring a sample having a known resistivity of 0.0216 ohms per square. Lift-off curve R is a graph of a polynomial function of form $Y=-(K)-(L)X+(M)X^2$, where Y is quadrature voltage in units of Volts, X is in-phase voltage in units of Volts, and K, L, and M are constants. Processor 12 identifies this second order polynomial function as the one which best fits the measured voltage pairs.

In most cases, twenty-five (or a number on the order of twenty-five) sense coil voltage pairs are sufficient to characterize each lift-off curve with adequate precision. The range of probe positions (along the z-axis) over which measurements are made is proportional to the sample's conductivity (greater probe-to-sample separations are generally required for samples of greater conductivities), and depends also on the probe radius. As a rule of thumb (for a typical sample), the maximum probe-to-sample separation needed to determine a lift-off curve is substantially equal to 50% of the drive coil radius. We prefer to discard (or avoid measuring) sense coil voltage pairs for very large probe-to-sample separations, to avoid unnecessary processing of data that will not contribute significantly to an accurate lift-off curve determination.

Returning to the FIG. 2 example, each of lift-off curves A through H is determined by the same process employed to determine above-described curve A (one lift-off curve A through H for each of eight samples having a different known resistivity). The sample resistivities (in ohms per square) associated with curves A through H, respectively, are 0.0216, 0.0263, 0.0525, 0.0699, 0.081, 0.16, 0.2597, and 0.39.

After determining a set of reference lift-off curves (e.g., curves A–H shown in FIG. 2), processor 12 performs the next step of the inventive method by determining a set of "intersection" voltage pairs, each intersection voltage pair representing the intersection of a different one of the reference lift-off curves with a "selected" curve (which can be, for example, a circular arc or another graph of a polynomial function) in X–Y voltage space, where X represents in-phase voltage and Y represents quadrature voltage. One such "selected curve" (circular arc V) is shown in FIG. 2. Selected curve V is a semicircle centered at X= 0 volts and approximately Y= −0.8 volts. Alternatively, another selected curve could have been employed, such as a circular arc centered at the origin (Y= 0 volts, X=0 volts).

The "X,Y" coordinates of point A1 along lift-off curve A are an example of such an intersection voltage pair for "selected" curve V.

After processor 12 determines a set of intersection voltage pairs along a selected curve, processor 12 implements the next step of the inventive method which is to determine a functional relation between the known conductivity associated with each intersection voltage pair and the selected curve (referred to below as a "conductance function"). The conductance function determines a conductivity value for each point on the selected curve, including conductivity values not associated with any of the reference lift-off curves. For example, point Z on selected curve V corresponds to a unique conductivity (determined by processor 12 from the conductance function for selected curve V) that is greater than 0.0263 ohms per square (associated with lift-off curve B) and less than 0.0525 ohms per square (associated with lift-off curve C). In a class of preferred embodiments, processor 12 stores a conductivity value, determined by the conductance function, for each of many different points (index voltage pairs) on the selected curve in memory 14 as a look-up table. Each such conductivity value can be retrieved from the stored look-up table by accessing the memory location indexed by the corresponding index voltage pair.

In variations on the described method, a conductance function relating a known conductance (rather than a conductivity) of each measured sample to an intersection voltage pair on the "selected" curve, or a "resistance function" or "resistivity function" relating a known resistance or resistivity of each measured sample to an intersection voltage pair on the "selected" curve, can be determined and processed as a substitute for the above-described conductance function. For convenience, the expression "conductance function" is used herein (including in the claims) in a broad sense to denote any such conductance function, resistance function, or resistivity function, or any function which relates a known conductance, conductivity, resistance, resistivity, sheet resistance, or sheet conductance of each of a set of measured samples to an intersection voltage pair on a "selected" curve, as well as a narrowly defined conductance function (relating a known conductance of each of a set of measured samples to an intersection voltage pair on a "selected" curve).

Figure 4:
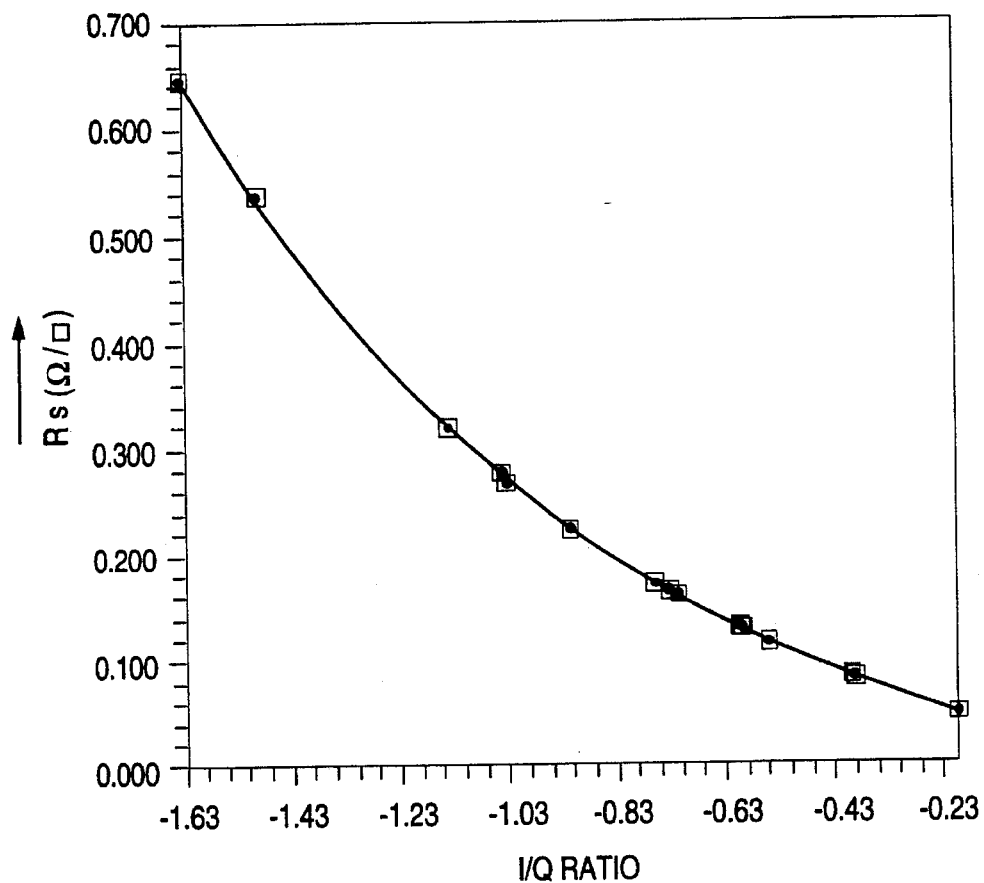
FIG. 4 is a graph of a conductance function which relates a sheet resistance to each point on a "selected curve" of the type employed in performing the inventive method (curve "V" in FIG. 2 is an example of such a selected curve).

FIG. 4 is a graph of a conductance function which determines a sheet resistance, $R_s$ (in units of ohms per square), for each point on a selected curve of the type employed in performing the inventive method. The horizontal axis of FIG. 4 identifies each point on the selected curve by an I/Q ratio, where "I" represents in-phase voltage in a sense coil and "Q" represents quadrature voltage in the sense coil. A set of sheet resistance values from the conductance function of FIG. 4 can be stored as a look-up table (of the type described above), with each look-up table entry being indexed by a corresponding index voltage pair (I/Q ratio).

With reference again to FIG. 2, after the described look-up table has been stored in memory 14, the conductivity of an "unknown" sample can be determined in accordance with the invention in the following manner. A lift-off curve is generated by producing an AC voltage in drive coil 4 while employing meter 10 to measure both in-phase and quadrature components of the AC voltage induced in sense coil 6, for each of a number of probe positions along the z-axis relative to the unknown sample, in the same manner as described above with reference to generation of a reference lift-off curve. As during reference lift-off curve generation, the separation between the sample and the probe (along the z-axis) need not be measured or otherwise known.

The measured sense coil voltage pairs (each pair comprising an in-phase voltage and a quadrature voltage) are processed in processor 12 to determine a lift-off curve (in the same manner as similar data for a reference sample are processed to determine a reference lift-off curve). Specifically, processor 12 processes the output signal from meter 10 for each of several probe positions to determine a polynomial function (a function of "in-phase" voltage versus "quadrature" voltage) which best fits the data. This function determines the lift-off curve for the unknown sample.

Processor 12 next determines an intersection voltage pair (identified as a "new intersection voltage pair" below in this paragraph) which represents the intersection of the lift-off curve (for the unknown sample) with the "selected" curve employed during look-up table generation (data determining the "selected" curve will have been prestored in a memory within processor 12 or in external memory 14). Processor 12 then identifies the conductivity of the unknown sample as the look-up table value it retrieves from the memory location of memory 14 which is indexed by the new intersection voltage pair. If the new intersection voltage pair is not equal (or approximately equal) to one of the index voltage pairs which index a stored look-up table value, then an interpolation operation can be performed to determine the conductivity of the unknown sample. Such interpolation operation could be performed by retrieving the two stored look-up table values indexed by the two index voltage pairs which most closely match the new intersection voltage pair, and then interpolating between these two retrieved look-up table values.

In alternative embodiments, software for implementing the conductance function itself can be stored (rather than the described look-up table) in memory 14. In such alternative embodiments, the conductivity of an unknown sample can be determined in the following manner. A lift-off curve is generated by producing an AC voltage in drive coil 4 while employing meter 10 to measure both in-phase and quadrature components of the AC voltage induced in sense coil 6, for each of a number of probe positions along the z-axis relative to the unknown sample, in the same manner as described above with reference to generation of a reference lift-off curve. The measured sense coil voltage pairs are then processed in processor 12 to determine a lift-off curve (in the same manner as similar data for a reference sample are processed to determine a reference lift-off curve). Processor 12 next determines an intersection voltage pair which represents the intersection of the lift-off curve (for the unknown sample) with the "selected" curve employed during look-up table generation (data determining the "selected" curve will have been prestored in a memory within processor 12 or in external memory 14). Processor 12 then determines the conductivity of the unknown sample by processing the intersection voltage pair in accordance with the conductance function.

It should be appreciated that, even in the alternative embodiments described in the previous paragraph, there is no need to measure (or know) the separation between the eddy current probe and the sample.

Figure 6:
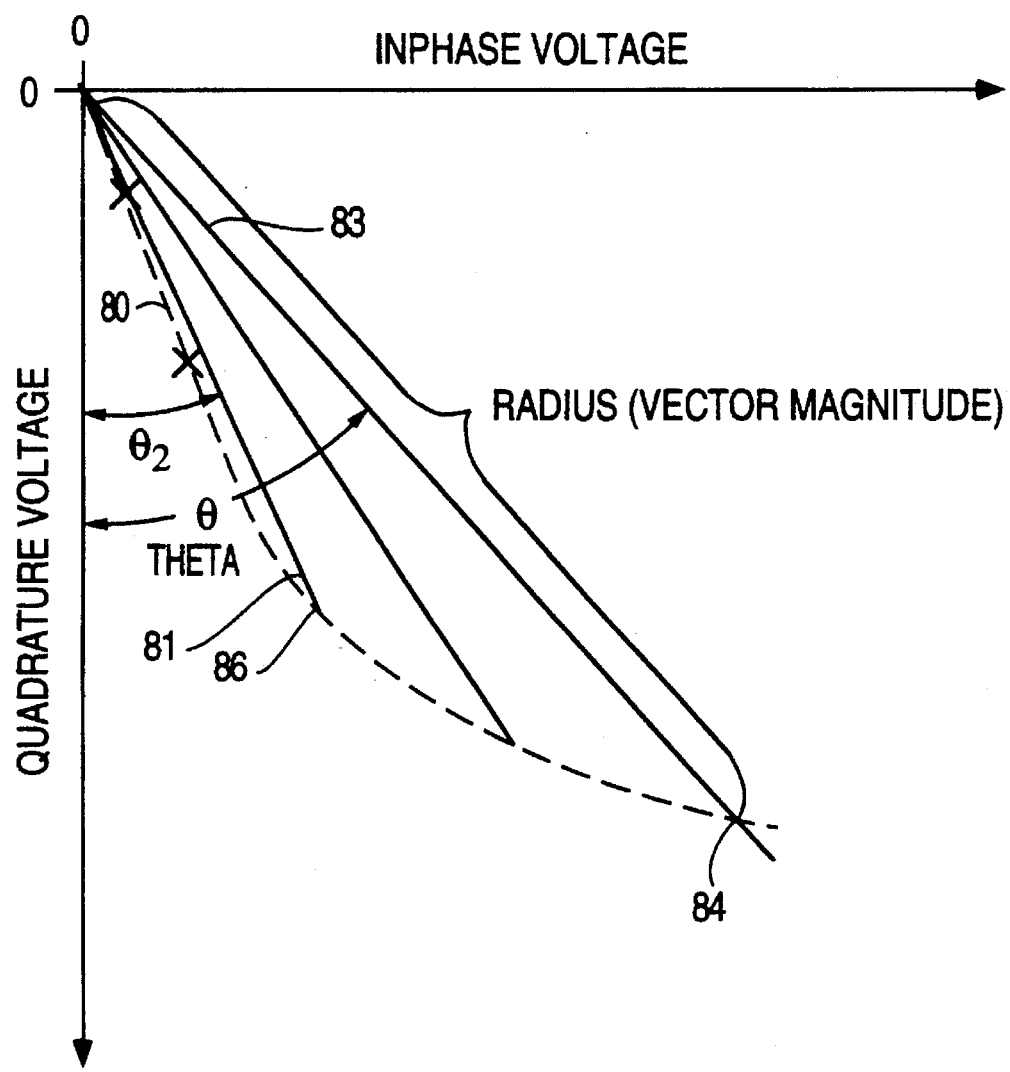
FIG. 6 is a graph of a lift-off curve, and rays intersecting the lift-off curve.

In variations on the embodiment described with reference to FIG. 2, points along the lift-off curves generated in performing the invention are characterized by polar coordinates (an angular coordinate θ and a radial coordinate R), rather than rectangular coordinates in voltage (in-phase and quadrature) space. For example, lift-off curve 80 is graphed in FIG. 6 in rectangular (in-phase and quadrature) voltage space, but its points can alternatively be characterized by polar coordinates. Thus, point 84 along lift-off curve 80 in FIG. 6 has a radial coordinate equal to the length of ray 83 (from the origin to point 84) and an angular coordinate θ as shown in FIG. 6. Similarly, point 86 along lift-off curve 80 has a different radial coordinate equal to the length of ray 81 (from the origin to point 86) and a different angular coordinate $θ_2$ as shown in FIG. 6.

Figure 7:
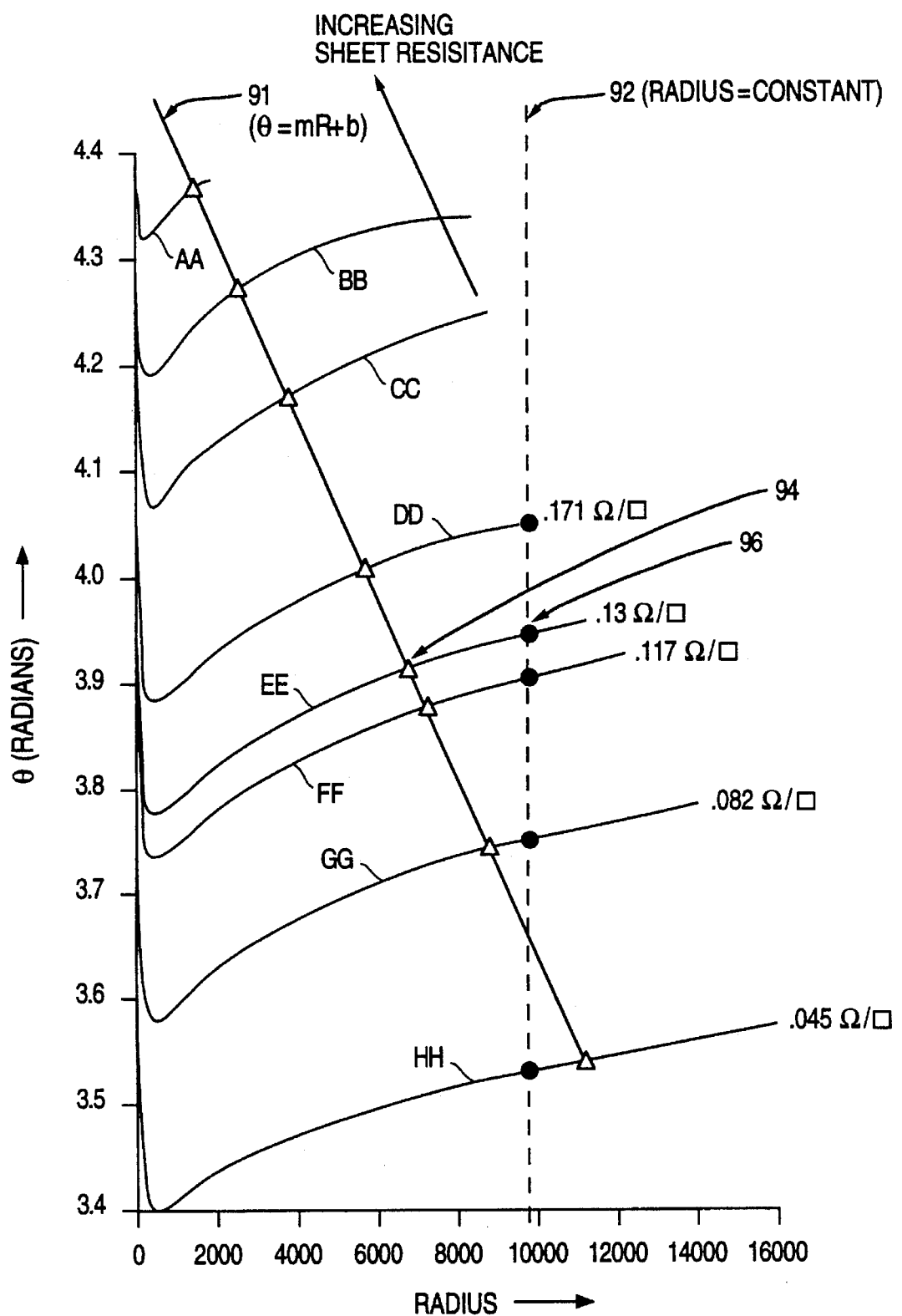
FIG. 7 is a graph of eight lift-off curves (plotted in polar coordinates), and two "selected curves" intersecting the lift-off curves, generated in accordance with an embodiment of the look-up table generation operation of the invention.

In performing one such variation, each of reference lift-off curves AA through HH (of FIG. 7) is determined by the same process employed to determine above-described lift-off curves A through H of FIG. 2 (by measuring eight samples having different known resistivities). However, FIG. 7 shows the lift-off curves plotted in polar coordinates since in this variation, processor 12 determines lift-off curves AA through HH by processing data indicative of polar coordinate representations of measured (in-phase versus quadrature) voltage pairs in a sense coil. The sample resistivities (in ohms per square) associated with reference lift-off curves DD through HH are 0.171, 0.13, 0.117, 0.082, and 0.045, respectively.

After determining reference lift-off curves AA–HH of FIG. 7, processor 12 performs the next step of the inventive method by determining a set of "intersection" voltage pairs, each intersection voltage pair representing the intersection of a different one of the reference lift-off curves with a "selected" curve (which can be, for example, line 91, line 92, a graph of another polynomial function, or a graph of some other complex function) in R-θ space, where radial coordinate R satisfies $R = (X^2 + Y^2)^{1/2}$, with X representing in-phase voltage and Y representing quadrature voltage, and θ is an angular coordinate. "Selected" curve 92 in FIG. 7 is a line of constant radial value R in R-θ space, and "selected" curve 91 in FIG. 7 is a line θ = mR+ b (where m and b are constants) in R-θ space. We have found that data processing in accordance with the invention is typically much simpler if the lift-off curves and intersection voltage pairs are characterized (by the processor) in terms of polar coordinates in R-θ space (rather than rectangular coordinates in X–Y space), principally since suitable "selected" curves can be defined very simply in such an R-θ space.

Figure 8:
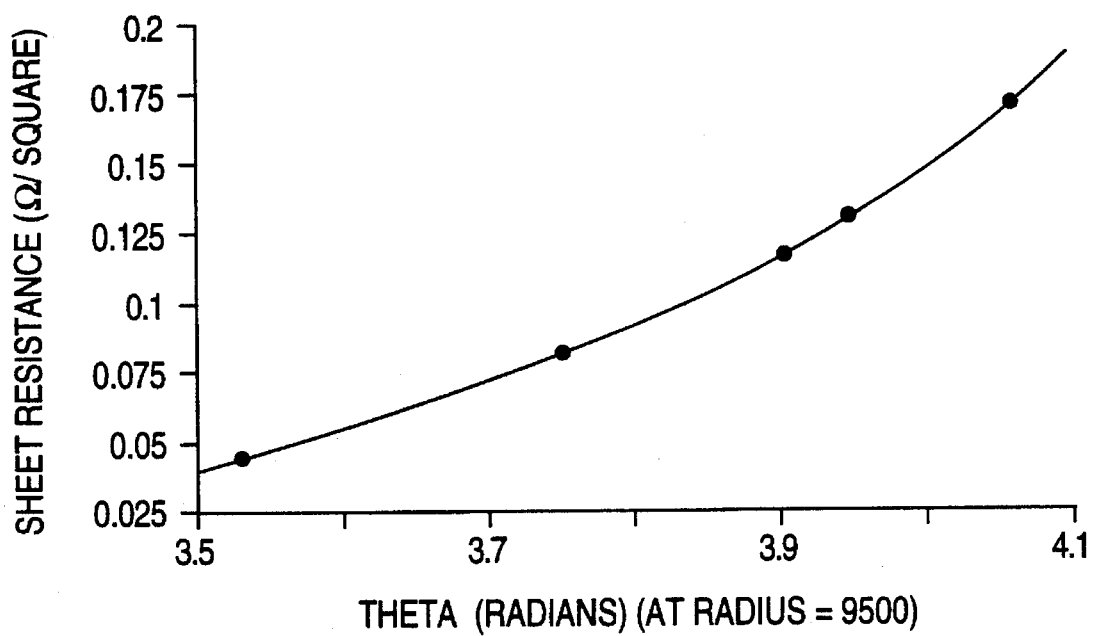
FIG. 8 is a graph of a conductance function which relates a sheet resistance to each point on a "selected curve" of the type employed in performing the inventive method.

The "R,θ" coordinates of point 94 along lift-off curve EE are an example of an intersection voltage pair for selected curve 91, and the "R,θ" coordinates of point 96 along lift-off curve EE are an example of such an intersection voltage pair for selected curve 92. After processor 12 determines a set of intersection voltage pairs along a selected curve, processor 12 implements the next step of the inventive method which is to determine a "conductance function" which is a functional relation between the known conductivity associated with each intersection voltage pair and the selected curve. FIG. 8 is a graph of such a conductance function which relates a sheet resistance to each point on a "selected curve" of the type employed in performing the embodiment of the inventive method described with reference to FIG. 7.

A preferred embodiment of a portion of the FIG. 1 apparatus will next be described with reference to FIG. 3. Sample 2, to be measured by the eddy current probe within probe housing 28, rests on a magnetically shielded stage comprising member 33 (made of material having high magnetic susceptibility) and member 34 (made of electrically insulating material having low magnetic susceptibility) which supports member 33.

The eddy current probe comprises inner housing 23, drive coil 24 mounted within housing 23, and sense coil 26 mounted within housing 23. Sense coil 26 is mounted coaxially with coil 24, has a smaller radius than coil 24, and is astatically wound.

Outer probe housing 28, surrounding inner housing 23, is made of material having high magnetic susceptibility to provide magnetic shielding for coils 24 and 26 during the measuring process. Outer housing 28 is fixedly attached to probe arm 32. Preferably, arm 32 is made of electrically insulating material having low magnetic susceptibility. Linear actuator 40 is engaged with arm 32, for translating arm 32, housing 28, and the eddy current probe mounted within housing 28, together as a unit along the x-axis (parallel to the top surface of sample 2).

A linear actuator means is provided for translating housing 23 and coils 24 and 26 as a unit along the z-axis (the axis perpendicular to sample 2's top surface) relative to outer housing 28 and sample 2, while constraining motion of housing 23 in directions perpendicular to the z-axis (such as the direction of the x-axis of FIG. 3). One embodiment of such a linear actuator means includes identical linear actuators 35 and 36 (fixedly mounted in housing 28) and identical springs 30 and 31 (whose ends are attached between housing 23 and actuators 35 and 36, respectively). Arms 35a and 36a of actuators 35 and 36, respectively, push housing 23 (and thus coils 24 and 26) downward along the z-axis in response to appropriate control signals from control unit 15, thereby extending springs 30 and 31. In response to control signals from control unit 15 for retracting housing 23 (and coils 24 and 26) along the z-axis away from sample 2, actuators 35 and 36 enter a mode in which arms 35a and 36a retract (upward) and elongated springs 30 and 31 relax toward their equilibrium length, pulling housing 23 (and thus coils 24 and 26) upward along the z-axis. Alternatively, a linear actuator can be mounted between each of coils 24 and 26 and housing 23, for retracting one or both of coils 24 and 26 along the z-axis (relative to both housing 23 and sample 2) in response to control signals from control unit 15.

As in the FIG. 1 embodiment, AC voltage source 8 connected to drive coil 24 can be activated to produce AC voltage in coil 24, and meter 10 connected to sense coil 26 measures the induced AC voltage (both in-phase and quadrature components thereof) in coil 26 as a result of the AC voltage in claim 24 (and the influence of sample 2).

Preferably, the FIG. 3 apparatus includes a temperature sensor for measuring the temperature of sample 2 (or the portion of sample 2 near coils 24 and 26), and means for controlling the temperature of sample 2 (or the sample portion near coils 24 and 26). In one embodiment, the temperature sensor includes serpentine wire 50 positioned in a recess in the top face of stage member 33 to be in thermal contact with sample 2 (when sample 2 rests on member 33), and a temperature measurement circuit 52 electrically connected to wire 50. Circuit 52 monitors the resistance of wire 50 and generates (in response to an input signal indicative of wire 50's resistance) an output signal, T, indicative of sample 2's temperature.

The means for controlling the temperature of sample 2 can include a heating element 54 (which can have an annular shape as shown in FIG. 3) positioned in a recess in the upper surface of stage member 54, and a temperature control unit 56 which controls the rate of heat transfer from element 54 to sample 2 resting on member 33. Control unit 56 is preferably capable of causing element 54 to heat sample 2 to any temperature within a selected range over which conductance measurements are to be made.

Temperature sensors and temperature control means suitable for use in at least some implementations of the FIG. 3 embodiment are described in U.S. Pat. No. 5,260,558, issued Nov. 9, 1993, based on the U.S. patent application Ser. No. 07/897,459, filed Jun. 1, 1992, and assigned to the assignee of the present invention. The text of U.S. Pat. No. 5,260,668 is incorporated herein by reference.

Figure 5:
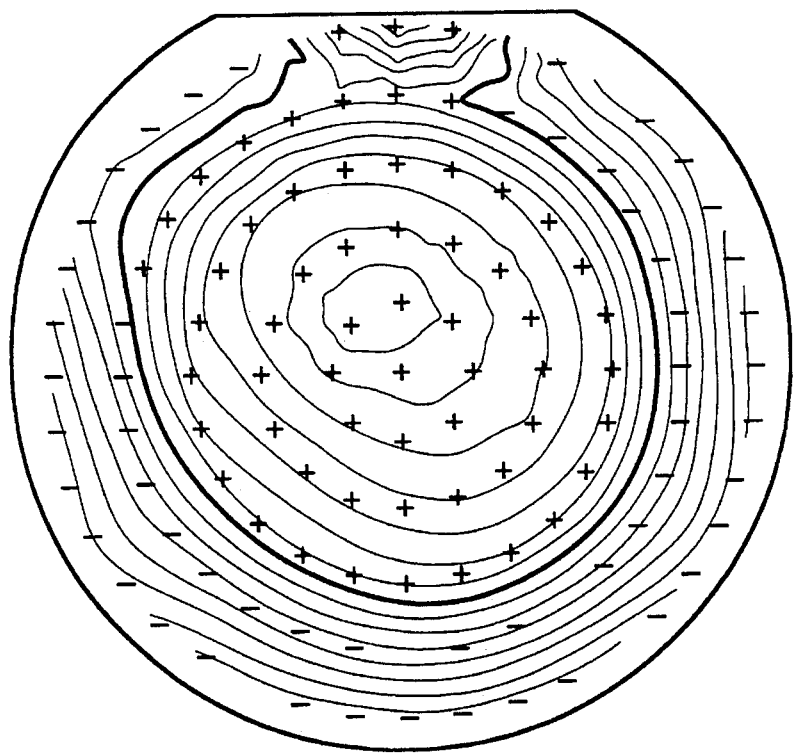
FIG. 5 is a contour map obtained by performing the inventive method at each of a plurality of locations on the surface of a disk-shaped sample.

A set of conductance measurements can be obtained by performing the inventive method at each of a pattern of locations on a sample surface. The resulting data can be plotted or displayed as a contour map of the type shown in FIG. 5, which represents data measured at a grid of locations on a disk-shaped semiconductor wafer. Each contour line of FIG. 5 indicates a common measured value of a parameter (e.g., conductance) measured in accordance with the invention.

Various modifications and alterations in the structure and method of operation of this invention will be apparent to those skilled in the art without departing from the scope and spirit of this invention. Although the invention has been described in connection with specific preferred embodiments, it should be understood that the invention as claimed should not be unduly limited to such specific embodiments.

What is claimed is:

1. A method for measuring conductance of a sample using an eddy current probe comprising a drive coil and a sense coil, including the steps of:
   (a) with the eddy current probe at a first separation from the sample, and with an AC voltage in the drive coil, measuring an induced voltage pair comprising in-phase and quadrature components of an induced AC voltage in the sense coil;
   (b) performing N repetitions of step (a), where N is a positive integer, with the eddy current probe at a different separation from the sample during each of said repetitions;
   (c) determining a conductance function relating conductance with location along the selected curve; and
   (d) after steps (a), (b), and (c), processing the induced voltage pairs obtained in steps (a) and (b) to generate a lift-off curve, determining an intersection voltage pair representing intersection of the lift-off curve with a selected curve, and determining the conductance of the sample from the intersection voltage pair and the conductance function.

2. The method of claim 1, wherein step (c) includes the steps of:
   (e) for each of several eddy current probe separations from a first reference sample of known conductance, and with an AC voltage in the drive coil, measuring an induced voltage pair comprising in-phase and quadrature components of an induced AC voltage in the sense coil, and processing said induced voltage pairs to generate a reference lift-off curve;
   (f) repeating step (e) for each of a number of different reference samples of known conductance; and
   (g) processing the reference lift-off curves generated during steps (e) and (f) to determine reference intersection voltage pairs representing intersections of the reference lift-off curves with the selected curve, and generating the conductance function from said reference intersection voltage pairs.

3. The method of claim 2, wherein the selected curve is a circular arc.

4. The method of claim 2, wherein the lift-off curve and the intersection voltage pair are determined by polar coordinates in an $R,\theta$ space.

5. The method of claim 4, wherein the selected curve is a line in said $R,\theta$ space.

6. The method of claim 2, also including the steps of:
   storing look-up table data, comprising conductance values determined by the conductance function for each of a number of different points on the selected curve, in indexed memory locations.

7. The method of claim 6, wherein step (d) includes the steps of determining the conductance of the sample by retrieving one of the conductance values from a memory location indexed by said intersection voltage pair.

8. The method of claim 6, wherein step (d) includes the steps of determining the conductance of the sample by:
   (h) retrieving two of the conductance values from memory locations indexed by index voltage pairs most closely matching said intersection voltage pair; and
   (i) interpolating between the two conductance values retrieved during step (h) to determine said conductance of the sample.

9. The method of claim 2, also including the step of storing software for implementing the conductance function, and wherein step (d) includes the step of:
   accessing the software to apply the conductance function to the intersection voltage pair, thereby generating a signal indicative of the conductance of the sample.

10. The method of claim 1, wherein the AC voltage in the drive coil has a frequency greater than one MHz.

11. The method of claim 1, wherein the sample is a portion of a semiconductor wafer.

12. The method of claim 1, wherein the sample is a portion of an integrated circuit.

13. The method of claim 1, wherein N is substantially equal to twenty-five.

14. An apparatus for measuring conductance of a sample having a surface, including:
- an eddy current probe comprising a housing, a drive coil mounted within the housing, and a sense coil mounted in close proximity to the drive coil in the housing;
- means for changing the separation between the eddy current probe and the surface of the sample;
- means for producing AC voltage in the drive coil;
- means for measuring an induced voltage pair resulting from said AC voltage in the drive coil at each of a number of different eddy current probe separations from the sample, wherein each said induced voltage pair comprises an in-phase component and a quadrature component of an induced AC voltage in the sense coil;
- a memory which stores data determining a conductance function relating conductance with location along the selected curve; and
- a processor connected with the memory and programmed with software for processing each said induced voltage pair to generate a lift-off curve, determining an intersection voltage pair representing intersection of the lift-off curve with a selected curve, receiving at least some of the data from the memory, and determining the conductance of the sample from said intersection voltage pair and said at least some of the data conductance function.

15. The apparatus of claim 14, wherein the drive coil is mounted coaxially with the sense coil.

16. The apparatus of claim 14, wherein the means for producing the AC voltage in the drive coil produces said AC voltage in the drive coil with a selected frequency in the range from about 100 KHz to at least about 100 MHz.

17. The apparatus of claim 14, wherein the processor is programmed with software for performing the following operations:
- (a) for each of several eddy current probe separations from a first reference sample of known conductance, and in response to said AC voltage in the drive coil, receiving an induced voltage pair comprising in-phase and quadrature components of an induced AC voltage in the sense coil, and processing said induced voltage pairs to generate a reference lift-off curve;
- (b) repeating step (a) for each of a number of different reference samples of known conductance; and
- (c) processing the reference lift-off curves generated during steps (a) and (b) to determine reference intersection voltage pairs representing intersections of the reference lift-off curves with the selected curve, and generating the data determining the conductance function from said reference intersection voltage pairs.

18. The apparatus of claim 17, wherein the selected curve is a circular arc.

19. The apparatus of claim 17, wherein the data determining the conductance function is look-up table data, and wherein the processor is also programmed with software for performing the following operations:
- storing the look-up table data in indexed memory locations in the memory, said look-up table data comprising conductance values determined by the conductance function for each of a number of different points on the selected curve.

20. The apparatus of claim 19, wherein the processor is also programmed with software for performing the following operations:
- determining the conductance of the sample by retrieving one of the conductance values from a memory location of the memory indexed by said intersection voltage pair.

21. The apparatus of claim 19, wherein the processor is programmed with software for determining the conductivity of the sample by:
- (d) retrieving two of the conductance values from memory locations of the memory indexed by index voltage pairs most closely matching said intersection voltage pair; and
- (e) interpolating between the two conductance values retrieved during step (d) to determine said conductance of the sample.

22. The apparatus of claim 14, also including:
- means for translating the eddy current probe parallel to the surface of the sample between measurement points along a scan path on the surface of the sample.

23. The apparatus of claim 14, wherein the eddy current probe also includes an outer housing, and wherein the means for changing the separation between the eddy current probe and the surface of the sample is a linear actuator means connected to the outer housing for translating the drive coil and the sense coil relative to outer housing in a direction normal to the surface, while constraining motion of the drive coil and the sense coil in directions parallel to the surface.

24. The apparatus of claim 14, wherein the eddy current probe also includes an outer housing made of material having high magnetic susceptibility, to provide magnetic shielding for the drive coil and the sense coil.

25. The apparatus of claim 24, also including:
- a probe arm fixedly attached to outer housing; and
- a linear actuator engaged with the probe arm, for translating said probe arm and the outer housing together as a unit in a direction normal to the surface.

26. The apparatus of claim 14, also including:
- sample temperature measurement means, including a sensor mounted in thermal contact with the sample.

27. The apparatus of claim 26, also including:
- a sample stage for supporting the sample, wherein the sensor is a serpentine wire mounted to the sample stage in a position so as to be in thermal contact with the sample.

28. The apparatus of claim 27, also including:
- a means for controlling temperature of the sample.

29. A method for measuring conductance of a sample using an eddy current probe comprising a coil, including the steps of:
- (a) with the eddy current probe at a first separation from the sample, and with an AC voltage in the coil, measuring an induced voltage pair comprising in-phase and quadrature components of an induced AC voltage in the coil;
- (b) performing N repetitions of step (a), where N is a positive integer, with the eddy current probe at a different separation from the sample during each of said repetitions;
- (c) determining a conductance function relating conductance with location along a selected curve; and
- (d) after steps (a), (b), and (c), processing the induced voltage pairs obtained in steps (a) and (b) to generate a lift-off curve, determining an intersection voltage pair representing intersection of the lift-off curve with the selected curve, and determining the conductance of the sample from the intersection voltage pair and the conductance function.

30. An apparatus for measuring conductance of a sample having a surface, including:

an eddy current probe comprising a housing and a coil mounted within the housing;

means for changing the separation between the eddy current probe and the surface of the sample;

means for producing AC voltage in the coil;

means for measuring an induced voltage pair resulting from said AC voltage in the coil at each of a number of different eddy current probe separations from the sample, wherein each said induced voltage pair comprises an in-phase component and a quadrature component of an induced AC voltage in the coil;

a memory which stores data determining a conductance function relating conductance with location along a selected curve; and a processor connected with the memory and programmed with software for processing each said induced voltage pair to generate a lift-off curve, determining an intersection voltage pair representing intersection of the lift-off curve with the selected curve, and determining the conductance of the sample from the intersection voltage pair and the conductance function.

* * * * *